United States Patent [19]
Wilson

[11] Patent Number: 5,358,479
[45] Date of Patent: Oct. 25, 1994

[54] MULTIFORM TWISTABLE TIP DEFLECTABLE CATHETER

[75] Inventor: James E. Wilson, Bound Brook, N.J.
[73] Assignee: Electro-Catheter Corporation, Rahway, N.J.
[21] Appl. No.: 163,326
[22] Filed: Dec. 6, 1993
[51] Int. Cl.[5] .................... A61M 37/00; A61M 25/00
[52] U.S. Cl. ...................... 604/95; 128/657; 128/772
[58] Field of Search ............... 128/4, 656, 657, 658, 128/772; 604/95, 164

[56] References Cited

U.S. PATENT DOCUMENTS

| | | | |
|---|---|---|---|
| 4,169,464 | 10/1979 | Obrez | 128/657 |
| 4,474,174 | 10/1984 | Petruzzi | 128/4 |
| 5,114,402 | 5/1992 | McCoy | 604/95 |
| 5,190,050 | 3/1993 | Nitzsche | 128/772 |
| 5,254,088 | 10/1993 | Lundquist et al. | 128/772 |
| 5,269,757 | 12/1993 | Fagan et al. | 604/95 |

*Primary Examiner*—C. Fred Rosenbaum
*Assistant Examiner*—Frank Wilkens
*Attorney, Agent, or Firm*—Cohen, Pontani, Lieberman, Pavane

[57] ABSTRACT

A steerable catheter including a handle and a catheter tube, the tip of which may be selectively curved by the operator to assume a pre-programmed curved shape in three dimensions. A single elongated, substantially flat planar shim is mounted within the tip of the catheter tube. The shim has at least one transverse or lateral twist which causes the tip of the catheter tube to assume a curvature in more than one plane when the catheter is operated by manipulation of the remotely positioned handle.

15 Claims, 9 Drawing Sheets

, 479

MULTIFORM TWISTABLE TIP DEFLECTABLE CATHETER

FIELD OF THE INVENTION

The present invention relates to vascular catheters for use in medical procedures and, most particularly, to catheters that can be remotely guided or steered by selective deflection of the catheter distal end or tip.

Catheters have been in common use in medical practice for many years. They are often used, for example, to probe locations inside a body lumen which are otherwise unreachable without surgery. A catheter is first inserted into a major vein or artery, or other body lumen, which is near the surface of the patient's body. The catheter is then guided to the area of concern by further inserting it into the body lumen. As medical knowledge increases, more uses of catheters have been developed and these uses have become more complex so that the ability to accurately and selectively steer the distally-located tip of the catheter has become of extreme importance. For example, there is a need to use steerable catheters to apply electrical pulses and the like to various internal, electrically excitable body tissues, such as the heart. Similarly, there is also a need to measure electrical currents existing in various body tissues and organs, such as the heart.

In order to place the tip of the catheter in the correct location and position, it is necessary to curve the tip of the catheter so that the catheter's distal end or tip will travel into the proper branch of a vascular lumen as the catheter is inserted. After the tip has been so curved, it is also often desirable to rotate the catheter's tip while maintaining the catheter tip's curvature so that the tip can then approach and contact the tissue of interest. In addition, once the catheter's tip has contacted the tissue of interest, it is also important that the tip make firm contact with the tissue so that an electrical current can be reliably applied by the catheter's tip to the tissue. Finally, it is desirable to be able to maintain the exact curvature of the catheter's tip during the procedure with a locking mechanism yet still permit ready, reliable and complete straightening of the catheter's tip upon command. It is also important to enable the user to selectively attain smooth, steady and predictable angular rotation of the tip as the handle or proximal end of the catheter is correspondingly rotated.

In known catheters, when the distal, curved tip must be rotated after encountering an obstruction, rotation of the proximally-located handle does not result in an equal, corresponding rotation of the catheter's distal tip until some threshold angular three or torque has thus been applied to the catheter base. At this point, the catheter tip can suddenly and uncontrollably spin in a jolt of rotation which, at the very least, reduces the angular resolution that is required by studies of the type normally undertaken with these devices.

A catheter which successfully addresses all of the above problems is disclosed in U.S. Pat. No. 5,190,050, the entire disclosure of which is expressly incorporated by reference herein. In the catheter there disclosed, the tip portion easily and reliably bends or twists in an angular orientation or curve that is selectively controllable and which can be securely locked in position. The tip or distal end of the catheter is hollow and has at least two flat planar rigid juxtaposed shims mounted therein. The distal ends of the shims are attached to one another while the proximal end of at least one of the shims is attached to a pull cable and ultimately to the catheter's handle. When a doctor or other user manipulates the handle so that the pull cable is drawn in the proximal direction, the tip of the catheter bends. Because of the planar shape of the shims and their rigidity, the bending of the catheter tip is always identical in direction, although varying in degree, and is in a single plane of movement. Also, because the shims are flat, rigid, and in sandwiched juxtaposition, when the handle of the catheter is steadily rotated, the distal tip of the catheter likewise rotates steadily without any jolts of rotation. The tip of the catheter can optionally have electrical contact plates to transmit electrical pulses to body tissue contacting the tip of the catheter.

Although the catheter disclosed in U.S. Pat. No. 5,190,050 is reliable, completely functional and useful for many applications, there are certain internal passages or chambers in the body which are not easily accessible to a catheter that can bend in only one plane. In the heart, for example, when it is desired to apply electrical pulses to the mitral or tricuspid valve annulus the tip of a catheter must be curved in two planes in order to properly contact the desired tissue. When the steerable catheter disclosed in U.S. Pat. No. 5,190,050 is used for this particular application, a doctor typically introduces the tip of the catheter into the heart's atrium and adjusts the catheter's handle to cause the tip to deflect in its single plane of deflection. The distal portion of the catheter's tip is then manipulated, either by rotation, by further insertion, or by a combination of both so that it contacts and is wedged against certain tissues and/or tissue walls within the heart. As a result, a proximate portion of the tip of the catheter, which does not contain the sandwiched juxtaposed rigid shims, is caused through such contact or abutment with tissue walls to assume a curve or bend in a plane that is different from the deflection plane of the distal end of the catheter's tip. As a result of this double twist in the catheter's tip, the catheter can then be further inserted so that it enters the mitral or tricuspid valve annulus. The second twist in the tip of the catheter, however, is not fixed or locked, is not readily controllable or selectively attainable, and is not pre-programmed into the catheter. As a consequence, the catheter tip manipulations needed to attain the desired catheter tip shape require substantial experience and skill. There is, therefore, a critical need for a steerable catheter that can easily and reliably attain a certain specific double or multiple plane twist when desired and under the selective control of a user.

SUMMARY OF THE INVENTION

The multiform twistable tip deflectable catheter of the present invention is directed to a catheter, the distal tip of which may be easily, reliably, selectively and remotely manipulated or bent and locked into a multiply curved condition using an attached proximally-disposed handle. The catheter of the invention comprises three primary portions: the catheter handle, the catheter tube, and the tip of the catheter tube.

Within the tip of the hollow catheter tube, one flat rigid shim is disposed. The distal end of the shim is attached to a pull cable with its proximal end terminated in a loop that, in turn, is attached to an anchor pin fixedly located within the catheter handle. The proximal end of the shim rests against the distal end of a guidewire spring extending within and along the catheter tube. The guidewire spring is mechanically connected to a longitudinally movable collar sleeve mounted on the body of the catheter handle. When the collar sleeve is selectively displaced, relative to the handle body and longitudinally toward the distal tip, the guidewire spring is likewise longitudinally displaced in the distal direction, carrying with it the shim. The shim advances longitudinally in the distal direction relative to the catheter handle body. However, the end of the catheter tube and the pull cable anchor the shim relative to the body of the catheter handle and prevents it from sliding longitudinally relative to the handle body. As a result, the tip of the catheter tube is caused to curve in a plane perpendicular to the plane of the shim. The tight fit of the rigid shim within the catheter tube ensures that the catheter tip will always curve in the same pre-programmed manner, and furthermore that this precise curve will remain stable even when external forces are applied to the catheter tip.

In order to cause the tip of the catheter to form a selectively-controllable curve in more than one plane, the shim is twisted laterally, i.e., across its width, in at least one place so that the shim has at least two portions that lie in different planes. As a result, the tip of the catheter, which bends in a direction perpendicular to the shim, correspondingly also bends in at least two planes. When the shim is given a single lateral twist so that one portion of the shim is twisted approximately 90° relative to the remainder of the shim, the tip of the catheter will attain a double or two-plane curve with one curve lying in a plane substantially perpendicular to the plane in which the other curve lies. Similarly, if the shim is given two twists at two respective positions along its length, the catheter will attain a triple or three-plane curve. The length of the portion of the shim before a twist is encountered determines the fully attainable length, extent and curvature of the curve—the longer the length of the shim section, the longer, more complete and more gradual the curve. Thus, by way of example, a short shim section will produce a gradual quarter circle or a tight full circle, while a long shim section will produce a gradual full circle or an even more gradual and larger radius quarter circle. Similarly, the amount of twist present in the shim will determine to what extent the planes of curvature of the catheter's tip are offset one from another. Additionally, the shim can be shaped so that it has a continuous twist along its entire length such that the flat planar shim resembles a helix. The three-dimensional shape of the catheter tip that results from a lateral twist along its entire length so that one end of the shim is twisted approximately 45° relative to the other end resembles that of a helix or cork screw. One or more collars, through which the pull cable slidably passes, are securely mounted at one or more points to the shim, preferably proximate the point at which the shim is twisted. The collars guide the pull cable and ensure that the pull cable does not become wedged between the shim and the inner surface of the outer shell of the catheter's tip.

The catheter tube is hollow, containing within its central lumen the guidewire spring. The outer shell of the catheter tube is preferably formed of a relatively rigid material, preferably with a wire braid embedded therein. An unreinforced section of catheter tubing is fixedly attached to the distal end of the reinforced tube so as to form the selectively deflectable tip portion. The structure of the catheter tube and of the enclosed guidewire spring render the catheter tube sufficiently rigid as to reliably transmit the relative longitudinal movement imparted by manipulation of the catheter's handle to the shim in the catheter tube's tip. Its relative rigidity further assures the ability to insert the catheter tube into a patient without any possibility that the catheter tube will buckle.

No specific form or structural configuration or operational attributes of the catheter handle are required, so long as the handle is capable of providing selective control of the elements in the catheter's tip: i.e. the guide wire, the shim and the guidewire spring. A curve or deflection that is selectively formed at or proximate the distal tip of the catheter may be locked in position and thereby retained by a locking mechanism in a preferred catheter handle. When the collar sleeve of the preferred catheter handle is translated longitudinally along the handle in the distal direction, a toothed lever mounted on the collar sleeve advances from one ratchet thread, cut into the body of the catheter handle, to the next ratchet thread where it is locked in place by the toothed lever which is urged into engagement with the thread by a resilient O-ring. To effectuate fine adjustment of the curvature of the catheter's tip, the collar sleeve is rotated relative to the handle body so that the toothed lever slides along grooves of the ratchet threads which have one or more helical grooves. These threads are preferably implemented as a single, continuous thread that extends helically about and along the handle. To reset and straighten the catheter tip, the toothed lever is depressed against the urgency of the resilient O-ring, thereby disengaging the lever's tooth from the ratchet thread. The force of the deflected catheter tip and the resiliency of the shim cause the shim to return to its untensioned, flat planar straight position, thereby straightening the catheter tip as the collar sleeve on the catheter handle is longitudinally displaced in the proximal direction to its initial starting position. The tension provided by the deflected catheter tip ensures that the catheter's distal tip portion reliably returns to its initial straight shape after the curve locking mechanism in the catheter handle is disengaged, thereby substantially eliminating hysteresis in the return of the catheter's tip portion to its original, non-deflected condition.

Furthermore, the planar, flat shape of the shim, combined with its rigidity and relatively tight fit within the catheter tube's outer shell, ensures that each section of the catheter's tip bends in only one orientation, i.e., perpendicular to the plane of that section of the shim.

The entire catheter tube, including its distal tip, can be easily and reliably rotated along its longitudinal axis by correspondingly rotating the catheter handle body about its longitudinal axis. The construction of the catheter tube, comprising its relatively rigid outer shell, its embedded wire braid and its guidewire spring, ensure that an axial rotation of the catheter handle reliably translates to an equal and gradually-effected axial rotation of the catheter tube's tip portion. In addition, the shim construction permits the entire tip portion to be rotated while still maintaining the exact user-selected curvature of the tip portion. Also, the structure of the steerable catheter of the present invention allows the catheter's tip portion to be pressed tightly against a patient's internal tissues by simply applying an appropriate longitudinal or rotative force to the catheter handle, even when the tip portion has been and remains curved.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

DETAILED DESCRIPTION OF THE PREFERRED EMBODIMENTS

Figure 1:
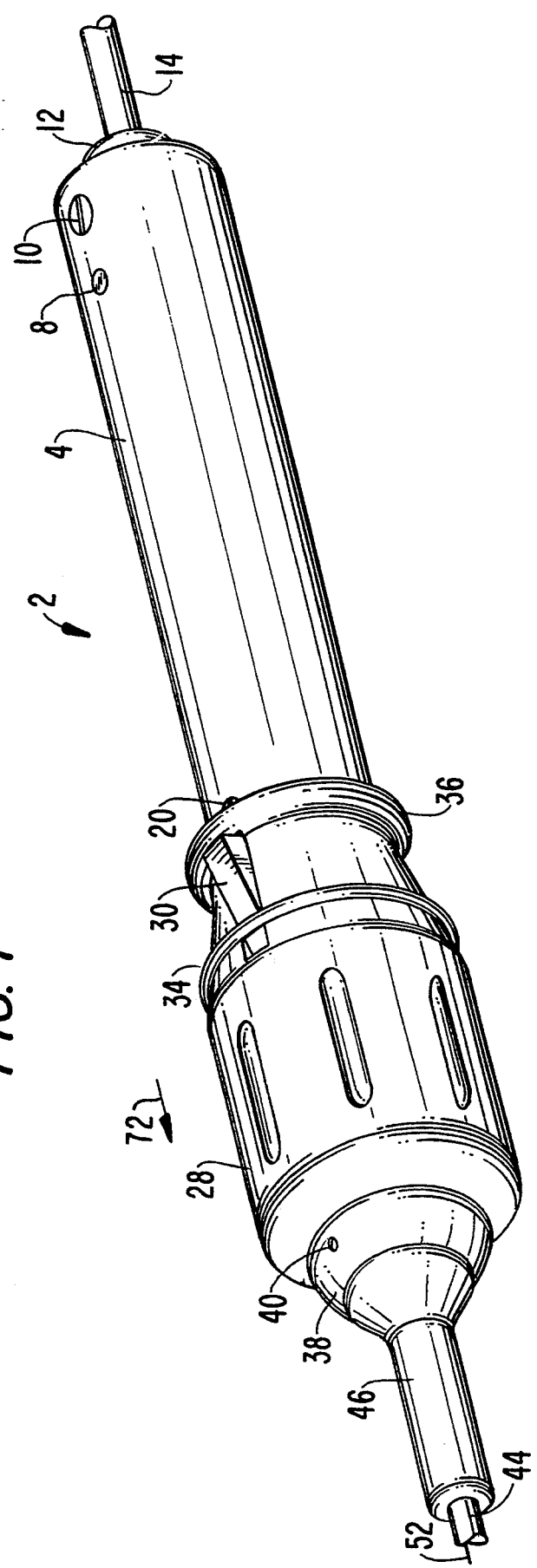
FIG. 1 is an elevated perspective view of the handle portion of a preferred embodiment of the multiform twistable tip deflectable catheter of the present invention.
Figure 2:
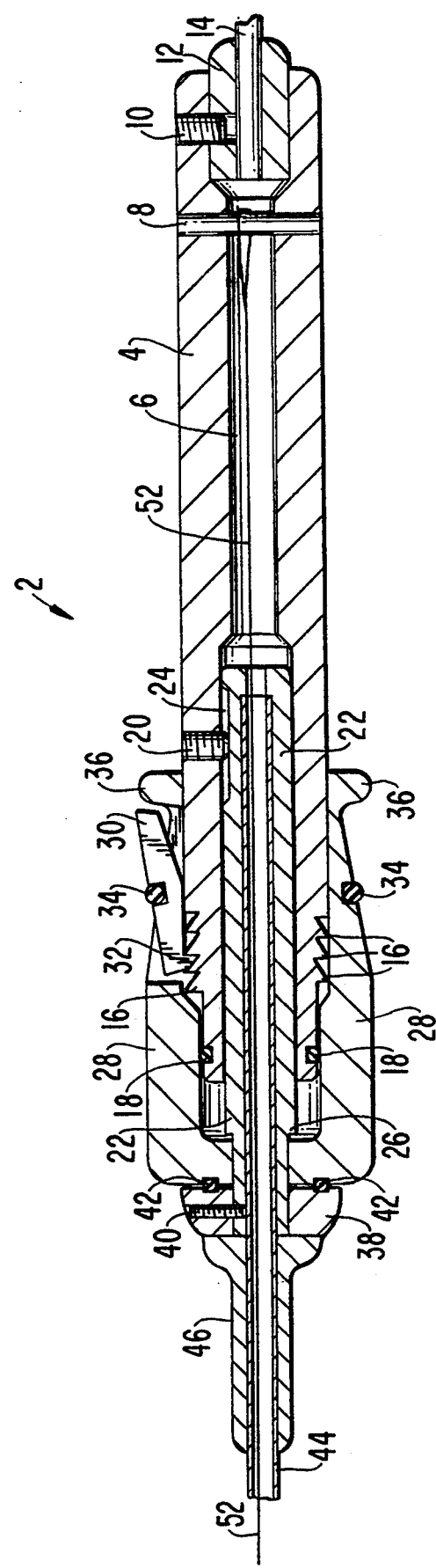
FIG. 2 is a longitudinal cross-sectional view of the handle portion of a preferred embodiment of the multiform twistable tip deflectable catheter of the present invention.

FIGS. 1 and 2 depict a preferred embodiment of a steerable catheter constructed in accordance with the present invention. The handle 2 of the catheter is comprised at its proximal end of a generally cylindrical body 4 having a central lumen 6 that extends longitudinally through and along the entire length of body 4. At the proximal end of body 4 are two lateral bores or holes. The first hole passes entirely through body 4 from its upper surface and through central lumen 6 to its lower outer surface. Within this hole an anchor pin 8 is securely mounted. The second hole passes from the outer surface of body 4 to central lumen 6 of body 4. A set screw 10 is threadedly mounted in this second hole and functions to engage and securely mount a plug 12 within the nearmost end of the central lumen 6 of body 4. Plug 12 includes an aperture with which set screw 10 engages. Plug 12 additionally has a longitudinally oriented central lumen into which an end tube 14, also provided with a central lumen, is securely mounted.

Body 4 is threaded proximate its forward (i.e. leftward in the Figures) or distal end with one or more helical ratchet threads 16 which circumscribe and corkscrew longitudinally along the outer surface of body 4. At the forwardmost end of body 4 is a circumferential groove into which is fitted an O-ring 18 formed of a resilient material, such as rubber. Near the longitudinal center of body 4 is a third lateral bore or hole into which is threadedly mounted a set screw 20. The hole in which set screw 20 is received passes from the outer surface of body 4 to the central lumen 6 of body 4. Base cylinder 22 is slidably mounted within the distal portion of the central lumen 6 of body 4 so that a portion of base cylinder 22 extends beyond the distal end of body 4.

Base cylinder 22 has a longitudinal central lumen that extends along its entire length and a longitudinal notch 24 at its rearward end. Base cylinder 22 is positioned within the central lumen 6 of body 4 so that set screw 20 engages and slides within the notch 24, and set screw 20 is of sufficient length and is screwed sufficiently deeply into body 4 so as to extend into notch 24. The forward end portion of base cylinder 22 is narrowed, forming a circumferential flange 26, and there is a lateral bore or hole defined in the forward, narrowed end of base cylinder 22 and passing from its outer surface to its central lumen.

A collar sleeve 28 is rotatably mounted onto the narrowed forward end of base cylinder 22 so that collar sleeve 28 abuts the flange 26 of base cylinder 22. Collar sleeve 28 is roughly cylindrical in shape with a central, longitudinally oriented lumen. As shown in FIG. 2, collar sleeve 28 and its central lumen are shaped so that the collar sleeve 28 surrounds a portion of the forward end of base cylinder 22 and the forward end of body 4, including ratchet threads 16. A longitudinal slot is cut through collar sleeve 28, into which slot is mounted an engagement lever 30. Lever 30 has a tooth 32 at its forward end for engagement with a ratchet thread 16 of the body 4. Although lever 30 is shown as having a single tooth 32 that engages a single thread 16, the lever 30 may alternatively have more than one tooth 32 for concurrent engagement with more than one thread or thread portion 16. Lever 30 further has a lateral groove which is aligned with a circumferential groove in collar sleeve 28 and into which is mounted an O-ring 34 formed of a suitably resilient material such as rubber. Lever 30 is shaped so that it defines a fulcrum portion in its lower surface for contact with an outer surface portion of the body 4. The lateral groove in lever 30 is positioned forwardly from the fulcrum portion of lever 30 so that O-ring 34 normally urges tooth 32 into engagement with a ratchet thread 16. As shown in FIG. 2, the ratchet threads 16 have rearward edges that slope at an angle of about 30° from the axis of central tureen 6 and forward edges that slope at an angle of about 90° so that the points of the ratchet threads 16 are about 60° in cross-section. However, in a more preferred embodiment, the tooth 32 of lever 30 will engage with enhanced reliability when the points of the ratchet threads 16 protrude forwardly, i.e. so that the rearward proximal edges of the ratchet thread 16 slope at about 30° and the forward edges at about 94°, each with respect to the central lumen axis, and the points of the ratchet threads 16 are about 56° in cross-section. The shape of the tooth 32 of lever 30 may also be appropriately modified for enhanced latching engagement with the threads 16. The rearward end of the collar sleeve 28 terminates in a flange portion 36.

Also mounted onto the narrowed forward end of base cylinder 22 is an end collar 38 which is roughly annular in shape. End collar 38 has a lateral bore or hole into which is mounted a set screw 40 that passes through end collar 38 into the hole at the distal end of base cylinder 22 to thereby secure and removably mount the end collar 38 to the base cylinder 22. Collar sleeve 28 and end collar 38 each have a respectively aligned annular groove in their abutting surfaces and into which is fitted an O-ring 42 formed of a resilient material such as rubber.

A catheter tube 44 fits into the forward end of the central lumen of base cylinder 22 and is secured therein by the set screw 40 which engages the outer surface of catheter tube 44. Tube 44 has a central lumen and is described in more detail below with particular reference to FIGS. 4, 5 and 6. Strain relief end 46 is fastened to catheter tube 44, as by an adhesive bond or the like, so that when catheter tube 44 is fully inserted and fixed within base cylinder 22, the strain relief end 46 contacts end collar 38. Strain relief end 46 is intended to minimize the effect upon handle 2 and its constituent elements of any flexing of the proximal end of catheter tube 44 during use of the catheter of the present invention and, in addition, provides a liquid-tight seal between the catheter tube periphery and the interior of the catheter handle assembly.

One end of a pull cable 52 is looped about the anchor pin 8 while the other end of the pull cable 52 passes through the central lumen of catheter tube 44 to its tip portion 54, as shown in FIGS. 3, 4, 5 and 6. Pull cable 52 is comprised of a material that is substantially or effectively nonstretchable when pulled longitudinally—such, for example, as the presently preferred stainless steel 302, with a gauge of about 0.009.

Figure 3:
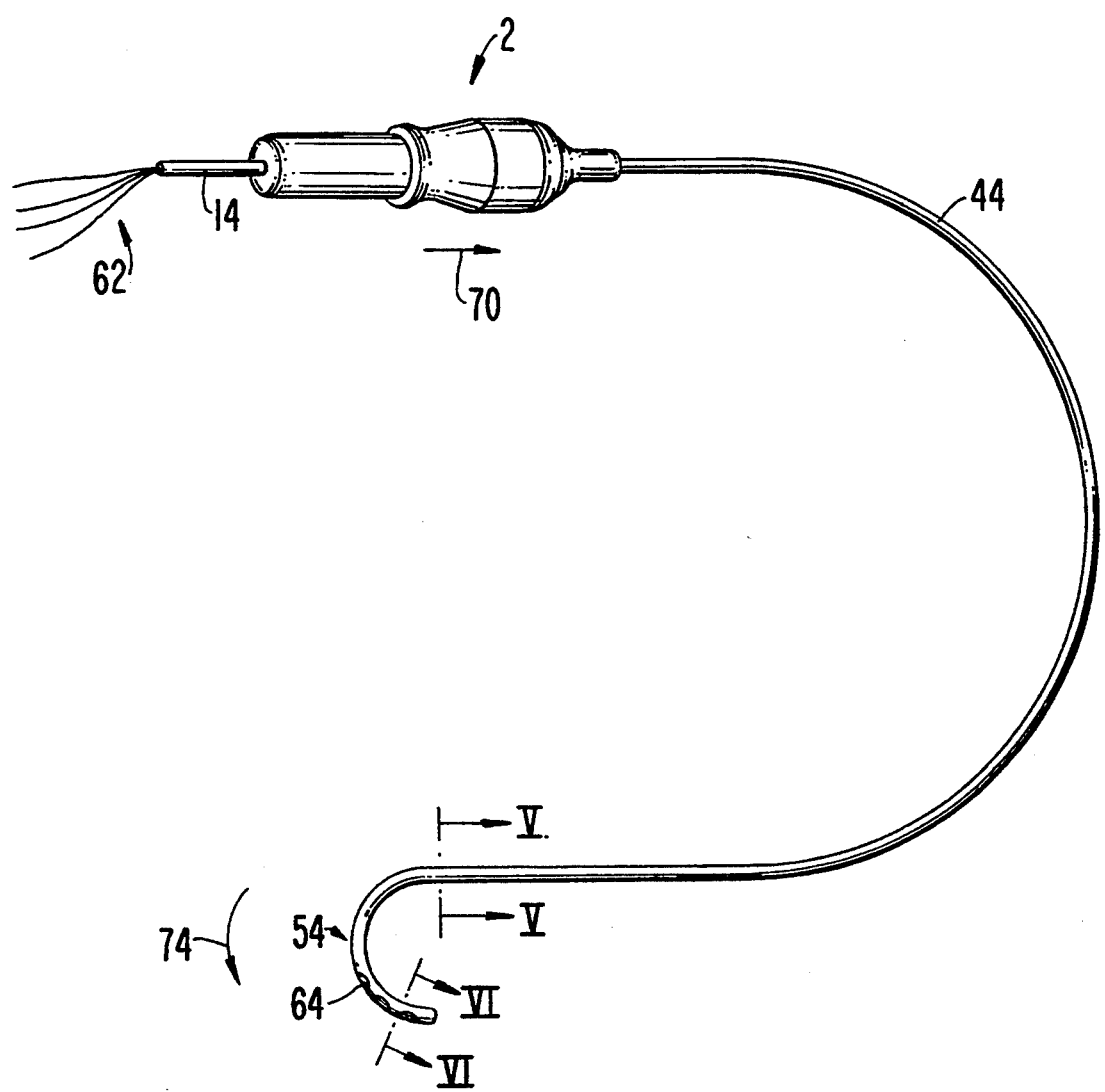
FIG. 3 is a simplified perspective drawing of a preferred embodiment of the multiform twistable tip deflectable catheter of the present invention.

Referring now to FIG. 3, catheter tube 44 has a length sufficient for it to be inserted through a patient's skin or body orifice and into a blood vessel or other body lumen or cavity or the like so that the deflectable tip portion 54 of catheter tube 44 can be controllably directed to and reach a particular point or location within the patient's body—as for example a location within the vascular system, such as the heart.

Figure 4:
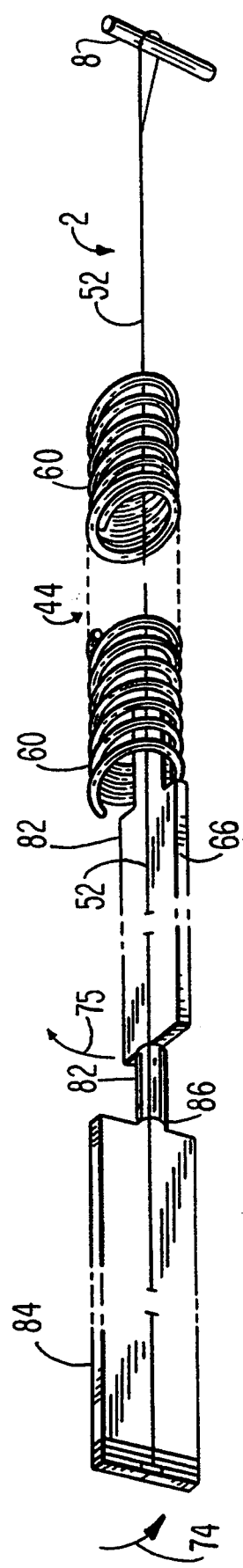
FIG. 4 is a simplified perspective drawing of the distally-located tip deflection mechanism, with the outer sleeve removed of a preferred embodiment of the multiform twistable tip deflectable catheter of the present invention.
Figure 5:
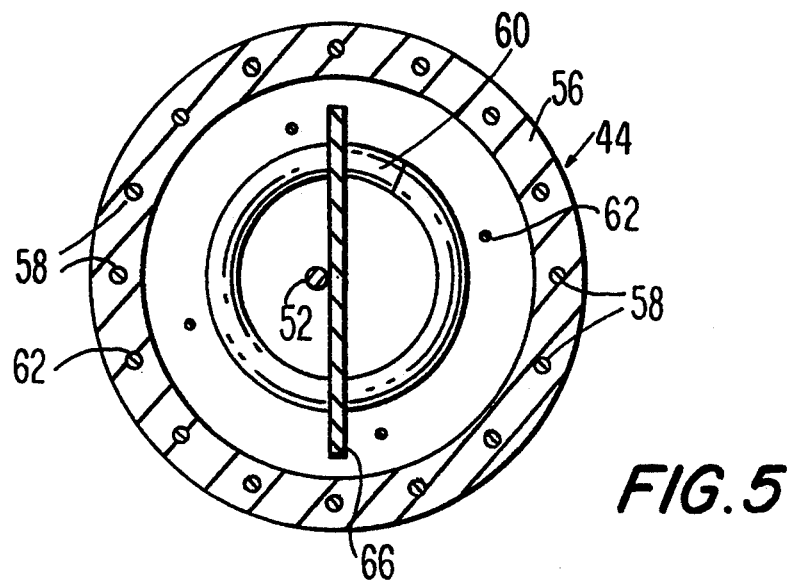
FIG. 5 is a cross sectional view of the catheter tube taken along the lines V—V in FIG. 3.
Figure 6:
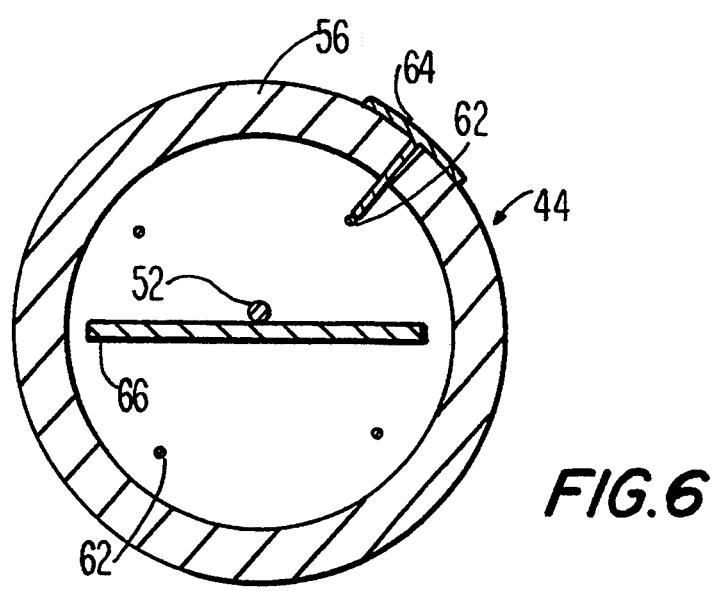
FIG. 6 is a cross sectional view of the catheter tube taken along the lines VI—VI in FIG. 3.

Referring particularly to FIGS. 4, 5 and 6, the catheter tube 44 is partially comprised of a hollow outer shell 56 formed of a rigid material, preferably by way of example a nylon coat polymer such as "Pebax" resin, manufactured by ATOChem. Outer shell 56 may also be comprised of vinyl, urethane or silicone. Catheter tube 44 preferably has a diameter of about 1 to 4 mm and a length of about 50 to 200 cm. In order to give the outer shell 56 of catheter tube 44 substantial effective rigidity and strength, a wire braid 58 is embedded into the outer shell. Wire braid 58 is preferably comprised of about 16 steel wires that are interwoven along the length of catheter tube 44. Wire braid 58 may, alternatively, be comprised of more or less than 16 wires and the wires may, alternatively, be comprised of a material other than steel such, illustratively, as fiberglass. The nylon coat polymer and wire braid 58 strengthen and support the structure of catheter tube 44 in the same way as concrete and embedded metal reinforcement rods or bars, respectively, are used in building construction.

Disposed radially within the central lumen of outer shell 56 of the catheter tube 44 is a guidewire spring 60 which provides columnar strength to the catheter tube. The size of guidewire spring 60 is selected so that its outer diameter is slightly less than the inner diameter of outer shell 56; the outer diameter of guidewire spring 60 is preferably about 40 to 70% of the inner diameter of outer shell 56. In one currently preferred embodiment the outer diameter of guidewire spring 60 is about 0.038 inches while the inner diameter of outer shell 56 is about 0.056 inches. Guidewire spring 60 is implemented as a long, tightly wound spring, preferably with a 0.012 inch pitch, and is disposed within and along almost the entire length of catheter tube 44, extending from the rearward end of base cylinder 22 to almost the rearward or proximal end of the tip portion 54 of catheter tube 44. A plurality of insulated electrical wire conductors 62 are disposed in the annular space defined between the outer shell 56 and guidewire spring 60. The electrical conductors 62 may, for example, have peripheral coatings that electrically insulate the electrical conductors 62 one from another and from the spring 60. One end of each of the electrical conductors 62 passes to a respective electrical contact plate 64 that is integrally carried on the outer surface of the outer shell 56 at or along the tip portion 54 of catheter tube 44. One electrical contact plate 64 is preferably disposed at the distal-most end of the tip portion 54 of the catheter tube 44 as shown in FIG. 3. The electrical conductors 62 pass through the entire length of catheter tube 44, through the central lumen in handle 2, and through and out of the end tube 14 where they may be separately connected to signal sensors or to an electrical power source (not shown) which can selectively provide electrical pulses or signals to one or more of the conductors 62. The outer shell 56 of the tip portion 54 of catheter tube 44 is preferably formed of relatively rigid material, as for example of the same resin family as is the outer shell of the non-tip portion of catheter tube 44; however, the outer shell 56 of tip portion 54 may, alternatively, be comprised of a lower durometer or "softer" material to increase its flexibility, so long as such material admits of firm attachment of the tip portion to the distal end of the proximally-disposed reinforced remainder of the catheter tube shell. In addition, it is preferred that the outer shell 56 of the tip portion 54 not include an interior wire braid, thereby facilitating its selective bendability or deflection under a user's control and permitting the incorporation of the electrode pads 64.

Referring now to FIGS. 4 and 5, the distal end of guidewire spring 60 contacts the elongated, rearward or proximal end portion 80 of a shim 66 that is disposed longitudinally within the tip portion 54 of catheter tube 44. Shim 66 is initially formed as an elongated, substantially flat plate and has a transverse width approximately equal to or greater than the outer diameter of guidewire spring 60, preferably about 40 to 70% of the inner diameter of the outer shell 56 of the tip portion 54, most preferably about 0.044 inches in width. Shim 66 preferably has a reduced width portion at its rearward end 80 that extends for a short distance into the central lumen of guidewire spring 60 and defines a pair flanges on opposite sides of the reduced width portion for abutment with the distal end of the spring 60. Guidewire spring 60 thus provides a seat for the shim 66. Alternatively, the proximal end 80 of shim 66 can be securely fastened, as by soldering, to the distal end of the guidewire spring 60. Shim 66 is relatively thin and is comprised of a material that is relatively rigid, such as stainless steel with a thickness of about 0.004 to 0.005 inches.

A central portion 82 of shim 66 is surrounded by a collar 82 which is fixedly attached, as by soldering, to shim 66 but shaped and sized so that pull cable 52 can freely slide between the shim 66 and collar 86. Collar 86 is also sized so that it contacts the inner surface of the outer shell 56. As a result, collar 86 does not restrict the longitudinal movement or displacement of pull cable 52 but constrains the deflection of shim 66 and pull cable 52.

As shown in FIGS. 4, 5 and 6, the distal end portion 84 of shim 66 has a lateral or transverse twist in its central portion 82 so that the distal end portion 84 is approximately perpendicular to proximal end 80 of shim 66. It is this lateral twist that enables the catheter tip to attain its multiple plane curvature. Alternatively, the lateral twist may be made in shim 66 at the proximal end of distal end portion 84 or at the distal end of proximal end 80.

The distal or forward end of pull cable 52 is securely fastened, as by soldering, to the distal end 84 of shim 66. In addition, pull cable 52 can be tightly wrapped around the distal end 84 of shim 66 and soldered. Furthermore, the distal end 84 of the tip portion 54 may be sealed with the material that forms the outer shell 56 of tip portion 54 to enclose the distal end 84 of shim 66 and thereby connect the shim distal end to the distal end of tip portion 54.

Where the catheter includes electrical signal sensing and/or applying pads or plates 64 or the like in or along the tip portion 54, the shim 66 may, as appropriate, be electrically insulated—such, for example, as by an insulating external surface coating—so as to prevent shorting to solder joints and the like.

In operation, the tip portion 54 of catheter tube 44 is first inserted into, for example, a patient's vessel such as a blood vessel or the urethra. The location of the tip portion 54 within the patient is typically monitored non-invasively as, for example, through the use of X-rays or sonography or the like. When the tip portion 54 of catheter tube 44 reaches a point in the body or vessel at which the tip portion must be precisely steered or directed, as at a point where two vessels meet or within a heart chamber, the tip portion 54 can be selectively caused to assume a curved or bent shape, as shown in FIG. 3, from its normally straight, generally linear disposition by the doctor or operator through activation of the catheter tip deflector control mechanism in handle 2. To do this, the operator holds the rearward portion of handle body 4 in one hand and, with his thumb, slowly pushes the flange portion 36 of collar sleeve 28 in the distal direction, i.e., in the direction of arrow 72 in FIGS. 1 and 2. As a result, collar sleeve 28 longitudinally slides and is displaced distally, together with end collar 38, base cylinder 22 and the guidewire spring 60 of catheter tube 44, all relative to the body 4. The distal movement of guidewire spring 60 effects likewise distal displacement of shim 66 within the tip portion 54 of catheter tube 44. However, the connection of the distal end of shim 66 to the catheter body 4 by pull cable 52 and the end of the substantially nonstretchable catheter tube 44 prevent any effective increase in the distance between the catheter's tip and the body 4 as the collar sleeve 28 is distally advanced. Because shim 66 is therefore unable to move distally relative to the body 4, shim 66 is caused to longitudinally bend in accordance with the amount of distal displacement applied to the collar sleeve 28. The generally flat shape of shim 66 causes the distal tip portion 84 of shim 66 and thus the distal portion 54 of catheter tube 44 to likewise bend in a direction perpendicular to the planar surface of the distal portion 84 of shim 66, such as in the direction of arrow 74 in FIGS. 3 and 4, and thereby assume a curved configuration in a first plane such as that shown in FIG. 3. Further sliding of the flange portion 36 of collar sleeve 28 in the distal direction, i.e., in the direction of arrow 72 in FIGS. 1 and 2, causes the proximate portion 80 of shim 66 to deflect in a direction perpendicular to the planar surface of the proximate portion 80 of shim 66, such as in the direction of arrow 75 in FIG. 4, and to assume a curved configuration in a second plane that is substantially pependicular to the first plane in which the distal portion 84 of shim 66 is curved. The transition between the two distinct curved deflections of the tip 54 of catheter tube 44 occurs proximate the collar 86 and twisted central portion 82 of shim 66.

As the collar sleeve 28 is displaced distally along the body 4 of handle 2, the tooth 32 of lever 30 rides up the rearward wall or face and thereby slips out of one ratchet thread 16 and into the next distally-succeeding ratchet thread. The resilience of the O-ring 34 permits pivoted movement of the lever 30 and then urges its tooth 32 to ride down into and to latch to this next succeeding ratchet thread 16 through its return urgency. As a result of this successive slipping and latching action, tooth 32 of lever 30 automatically locks the collar sleeve 28 in its distally displaced position even when the operator removes thumb pressure from the collar sleeve flange portion 36, thereby also locking and preserving the multiple twist or multiple plane curve attained by the tip portion 54 of catheter tube 44. By thus advancing the collar sleeve 28 in the distal direction, coarse adjustment of the curvature of tip portion 54 of the catheter tube is effected. To then attain a finer adjustment in the tip curvature(s) of the tip portion, the operator rotates the collar sleeve 28 about its longitudinal axis of rotation (which coincides with the central lumen 6 of body 4) relative to the handle body. As a result of this rotation of the collar sleeve 28, the tooth 32 of lever 30 rides along the helical ratchet thread 16 of body 4 effecting gradual, continuous and relatively minute longitudinal translation of collar sleeve 28 in the distally-advancing direction of arrow 72 or, alternatively for opposite sense rotation of the sleeve 28, in the proximally-withdrawing direction opposite that indicated by arrow 72, as appropriate or desired.

To thereafter rapidly or otherwise selectively straighten the tip portion 54 of catheter tube 44, lever 30 is depressed proximate its rearward end causing lever 30 to pivot on its fulcrum portion, thereby disengaging tooth 32 from ratchet thread 16. The return urgency or tension provided by the catheter tip with respect to collar sleeve 28 (through pull cable 52, shim 66, guidewire spring 60, base cylinder 22 and end collar 38) automatically causes, in response to the disengagement of tooth 32 from ratchet thread 16, return displacement of the collar sleeve 28 in the rearward or proximal direction, i.e. in the direction opposite that indicated by arrow 72, thereby rapidly (if desired) straightening tip portion 54 of catheter tube 44 to its initial straight shape. Alternatively, the tip portion 54 can be straightened slowly by rotating collar sleeve 28 in the appropriate direction, or by pivoting the lever 30 while grasping the sleeve 28 so as to permit its rearward return displacement in a selectively gradual manner.

As a consequence of the planar, flat shape of each of the several sections of the shim 66, and the relatively rigid material of which it is formed, it is virtually impossible for the tip portion 54 to bend in normal use in any direction other than substantially perpendicular or lateral to the planes of the proximate and distal portions 80, 84 of shim 66. The planar shape of the shim and its rigidity within the outer shell 56 also make it virtually impossible for the tip portion 54 to bend out of the preprogrammed planes of curvature once the curves have been locked into place by the latching or retention mechanism of the presently preferred control handle or, indeed, of any control handle providing the capability of retaining a particular selectively-effected deflection.

In use, it is often desirable to selectively rotate the entire catheter tube 44 through a desired angular adjustment after the desired curves in tip portion 54 have been attained and locked in place. Such a rotation may be readily and reliably achieved by selectively rotating the entire handle 2, through manipulation of the handle body 4 together with collar sleeve 28, about its longitudinal axis. The preferred rigidity and stability of the material and structure comprising the outer shell 56 of the catheter tube 44 and the supporting structure of the guide spring 60 allow such axial rotation of the handle 2 to be smoothly, directly and reliably transmitted to the tip portion 54 of catheter tube 44 without any unintended or unanticipated sudden rotational movements or jolts. Thus, a given axial rotation of handle 2 will result in a corresponding, equal axial rotation of catheter tube 44 anti a corresponding, equal rotation of its tip portion 54 while maintaining the latched curvature of tip portion 54. Gradual axial rotations of the tip portion 54 of up to or exceeding 360° can therefore be reliably achieved without sensitivity to rotational position through simple rotation of handle 2. Furthermore, the relatively rigid material forming the shim and its flat shape within the catheter's outer shell 56 are also effective to ensure reliable, steady rotation of the entire tip portion 54 without any sudden jolts of rotation while, at the same time, maintaining the locked curvatures of the tip portion 54.

Finally, it should be recognized that the rigidity of the material and structure of the catheter tube 44 and shim 66 allow the tube 44 to be strenuously urged longitudinally in the distal direction indicated by arrow 72 (FIG. 1) so as to firmly and aggressively press against and contact particular tissue within a patient's body, such as heart tissue, without risk that the catheter tube 44 or its tip portion 54 will buckle or unexpectedly deform.

As will be appreciated from the foregoing description, the longitudinally-oriented length of the notch 24 is selected so that the set screw 20 limits the longitudinal movement of base cylinder 22 (and therefore of collar sleeve 28 along the body 4), thereby also defining the bounds or limitations of curvature of the tip portion 54 of catheter tube 44. O-ring 18 ensures that body 4 slides uniformly and tightly through the center lumen of collar sleeve 28. O-ring 42 allows the end collar 38 to slide easily with and against the collar sleeve 28.

In addition, the use of set screws 10, 20 and 40, of O-ring 34 and of anchor pin 8 permits the handle to be readily assembled and disassembled for cleaning, adjustment or repairs.

The multiform twistable tip deflectable catheter of the present invention can be appropriately modified to create catheters with various different pre-programmed or selectively attainable multiple three-dimensional curves for various specific uses. The length of the portion of the shim 66 before a twist is encountered determines the length and extent of the curve—the longer the length of the shim section, the longer and more complete the curve. Thus, for example, a short shim section will produce a quarter circle, while a long shim section will produce a full circle. If the proximal portion 80 of shim 66 is short—such, for example, as about 0.75 inches—and the distal portion 84 of shim 66 is long—such, for example, as about 3.25 inches—when fully activated, the proximal portion of the catheter's tip will attain a quarter circle curve and the distal portion of the catheter's tip will attain a full circle. Similarly, the amount of twist in and between sections of the shim will determine to what extent the planes of curvature of the catheter's tip are offset one from another. One or more collars 86, through which pull cable 52 slidably passes, are securely mounted at one or more points to the shim, preferably proximate each point at which the shim is twisted, to ensure that the cable does not slip or otherwise move away from the flat surface of shim 66.

Figures 7A, 7B:
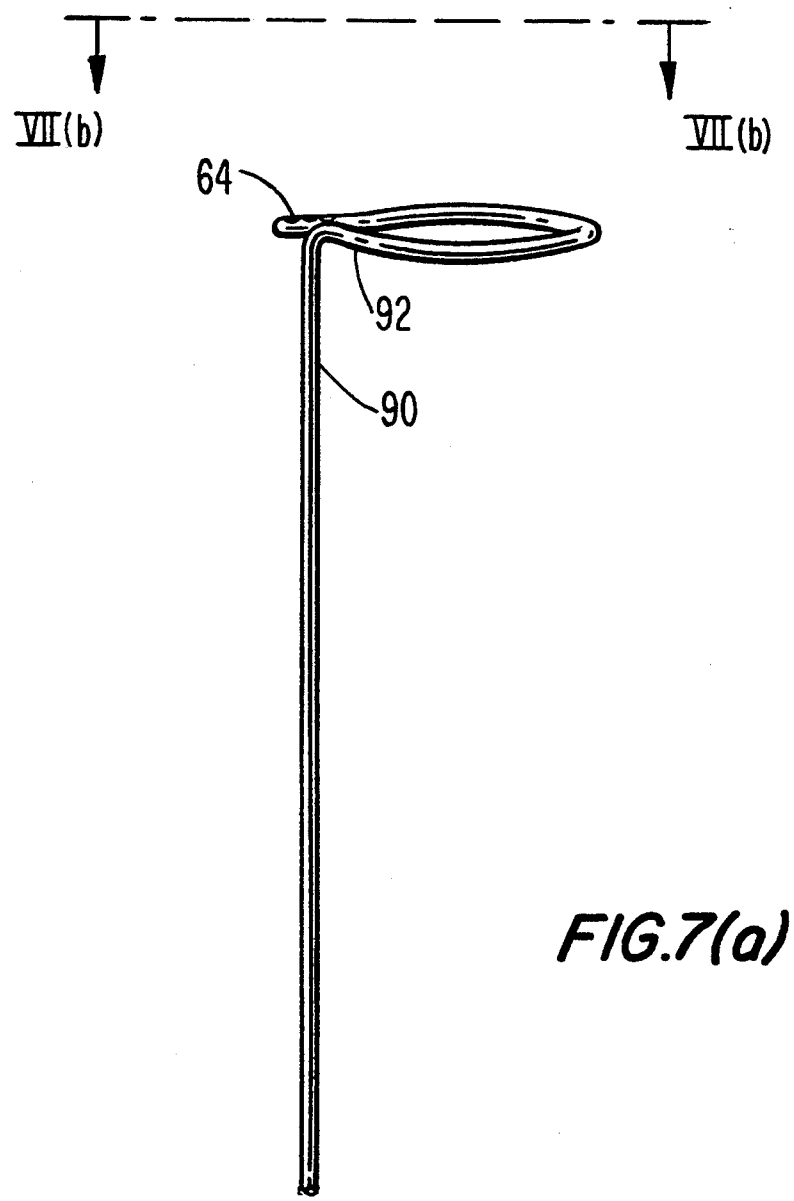
FIG. 7(a) is a side view and FIG. 7(b) is an end view of a first exemplary shape of the catheter tip attainable by a multiform twistable tip deflectable catheter constructed in accordance with the present invention.

FIG. 7 shows, by way of example, one shape of a catheter tip attainable by a multiform twistable tip deflectable catheter constructed in accordance with the present invention. The double twist shape shown is particularly useful in positioning catheter electrodes in the mitral or tricuspid valve annulus of the heart for mapping of electrical pathways. FIG. 7(a) is a side view of the catheter tip portion and FIG. 7(b) is an end view of that portion shown in FIG. 7(a) and taken along the lines VIIb—VIIb. It will be noted that the catheter tip has two distinct curves in two separate planes. The first curve is in a first plane and begins at point 90 and continues to point 92 where another curve begins in a plane that is rotated approximately 90° relative to the first plane. The curve in the first plane is a quarter circle, while the curve in the second plane is almost a complete circle. This catheter tip shape is produced by having a twist of about 90° in shim 66 at a proximal point along its length. A collar 82 is preferably positioned on shim 66 at the curve transition point 92. For this particular application, the full circle curve preferably has a diameter of about 35 mm; as a result, the distal portion 84 of shim 66 preferably has a length of about 110 min. The quarter circle curve in the proximal portion of the catheter's tip is attained by having the proximal portion 80 of shim 66 extend about 20 min.

Figure 8B:
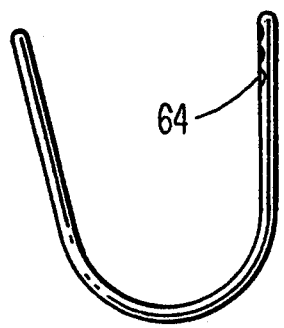
FIG. 8(b) is an end view and FIG. 8(c) is a second side view of a second exemplary shape of the catheter tip attainable by a multiform twistable tip deflectable catheter constructed in accordance with the present invention.
Figure 8C:
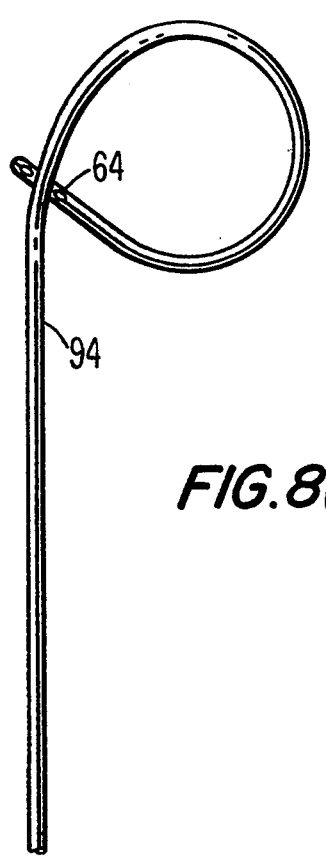
Figure 8A:
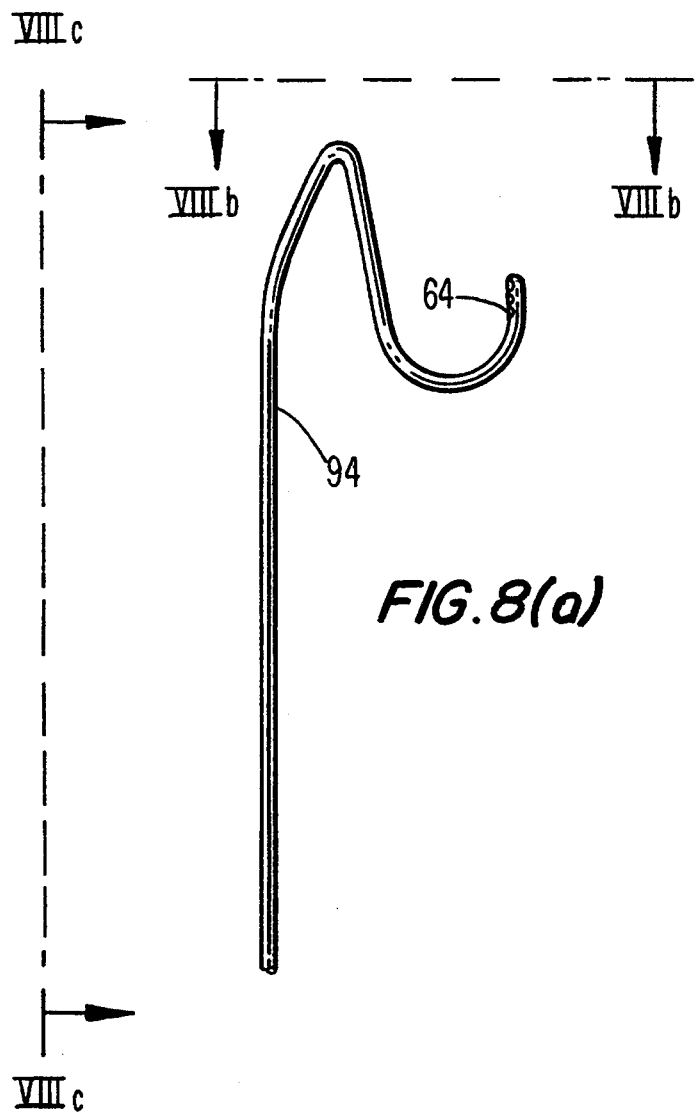
FIG. 8(a) is a first side view.

Another exemplary shape of a catheter tip attainable by a multiform twistable tip deflectable catheter in accordance with the present invention is shown in FIG. 8. This shape is similar to that of a helix or corkscrew and is particularly useful for accessing the ostium of the coronary sinus from an inferior approach. FIG. 8(a) is a side view of the catheter tip, FIG. 8(b) is an end view of the catheter tip portion shown in FIG. 8(a) taken along the lines VIIIb—VIIIb, and FIG. 8(c) is a side view of the catheter tip portion shown in FIG. 8(a) taken along the lines VIIIc—VIIIc. This catheter tip shape is produced by having a substantially continuous twist which begins at point 94 and continues along virtually the entire length of shim 66 so that one end of the shim is twisted approximately 45° relative to its other end. One or more collars 82 are preferably positioned along the length of shim 66 to confine the pull cable 52 so that it does not slip out of position when the catheter is caused to curve by user-controlled action upon the catheter's handle.

Figure 9B:
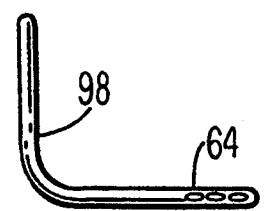
FIG. 9(b) is an end view and FIG. 9(c) is a second side view of a third exemplary shape of the catheter tip attainable by a multiform twistable tip deflectable catheter constructed in accordance with the present invention.
Figure 9C:
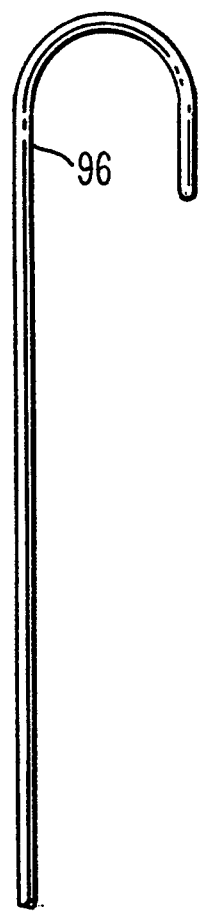
Figure 9A:
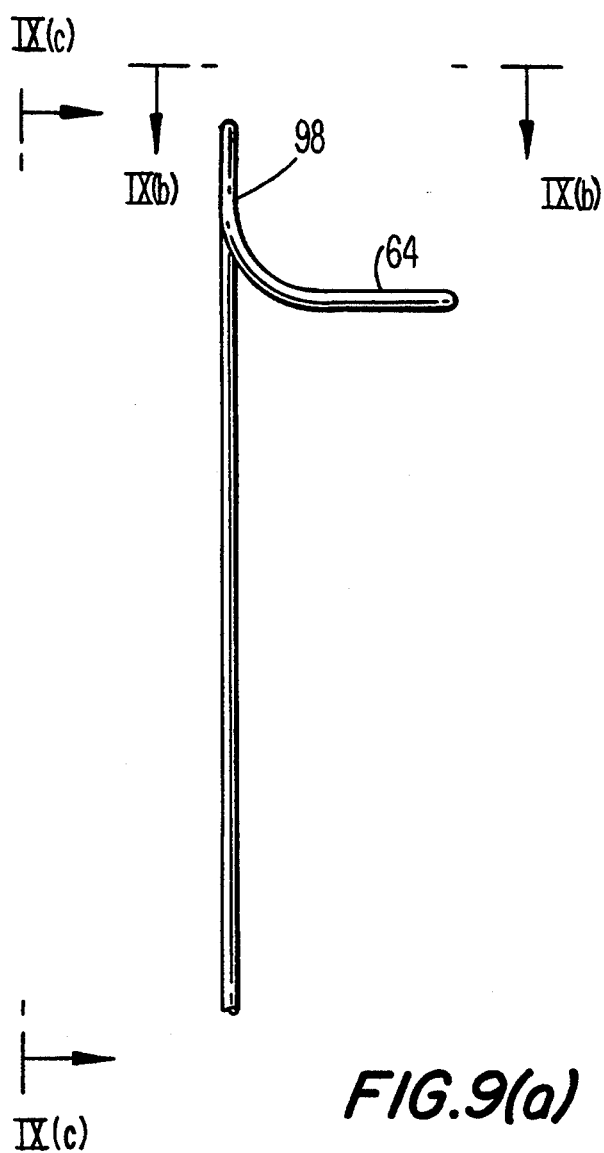
FIG. 9(a) is a first side view.

Another exemplary shape of a catheter tip attainable by a multiform twistable tip deflectable catheter in accordance with the present invention is shown in FIG. 9. This double twist shape is particularly useful for accessing the atrial septum of the heart with an orthogonal positioned tip for mapping or ablation procedures. FIG. 9(a) is a side view of the catheter tip, FIG. 9(b) is an end view of the catheter tip portion shown in FIG. 9(a) taken along the lines IXb—IXb, and FIG. 9(c) is a side view of the catheter tip portion shown in FIG. 9(a) taken along the lines IXc—IXc. The catheter tip has two distinct curves in two planes; the first curve is in a first plane and begins at point 96 and continues to point 98 where another curve begins in a plane that is rotated about 90° relative to the first plane. The curve in the first plane is a half circle, while the curve in the second plane is a quarter circle. This catheter tip shape is produced by having a twist of about 90° in the shim 66 at a substantially central point along its length. A collar 82 is preferably positioned on shim 66 at or proximate the curve transition point 98.

Figure 10B:
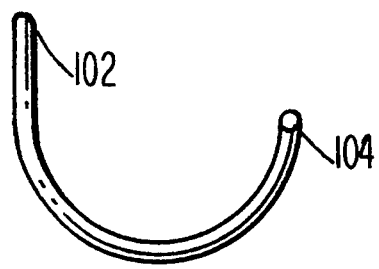
FIG. 10(a) is a side view and FIG. 10(b) is an end view of a fourth exemplary shape of the catheter tip attainable by a multiform twistable tip deflectable catheter constructed in accordance with the present invention.
Figure 10A:
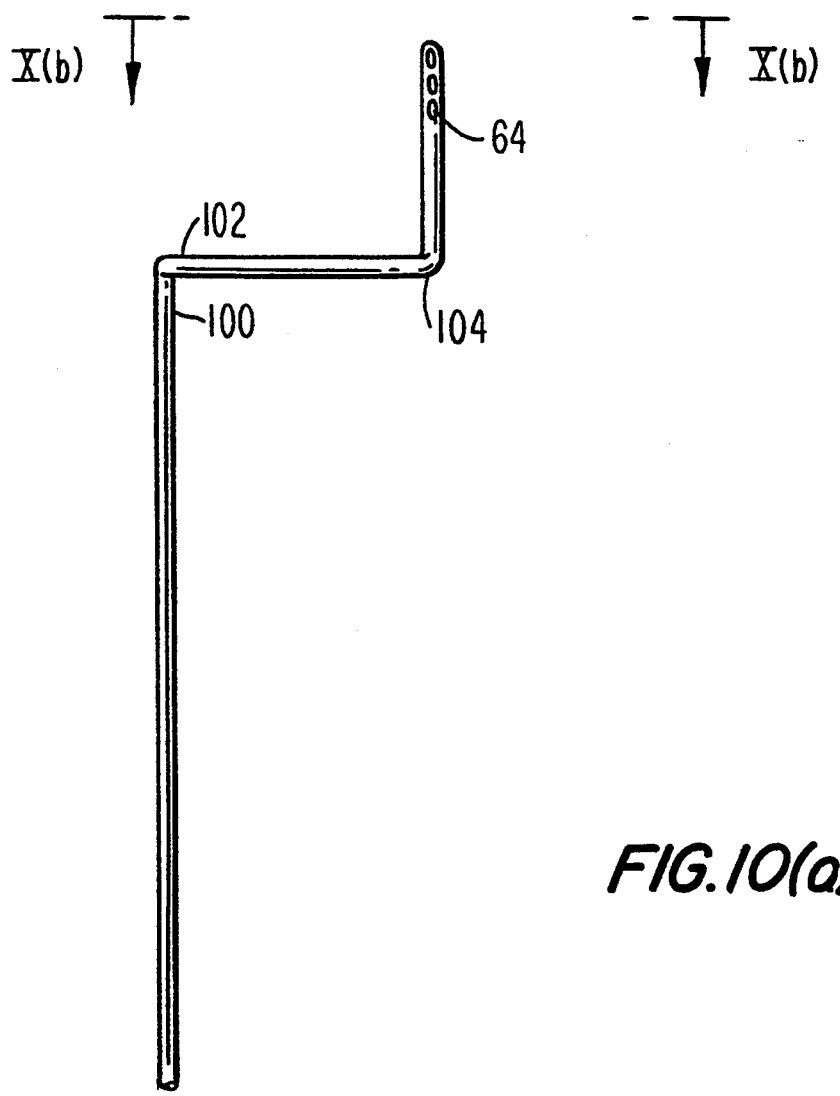

Yet another exemplary shape of a catheter tip attainable by a multiform twistable tip deflectable catheter in accordance with the present invention is shown in FIG. 10. FIG. 10(a) is a side view of the catheter tip and FIG. 10(b) is an end view of the catheter tip portion shown in FIG. 10(a) taken along the lines Xb—Xb. The catheter tip has three distinct curves in three distinct planes. The first curve is in a first plane and begins at point 100 and continues to point 102 where the second curve begins in a plane that is rotated about 90° relative to the first plane. The second curve continues to point 104 where the third curve begins in a plane that is rotated about 90° relative to the second plane. All three curves are approximately quarter circles. This catheter tip shape is produced by having two twists, each of about 90°, in the shim 66, one near the proximal end of shim 66 and one near the distal end of the shim. Two collars 82 are preferably positioned on shim 66 at the curve transition point 98. Although this particular catheter tip curve does not presently have a specific known or intended medical application, it demonstrates another type of pre-programmed curve that can be obtained using a catheter constructed in accordance with the present invention.

Thus, while there have been shown and described and pointed out fundamental novel features of the invention as applied to several preferred embodiments thereof, it will be understood that various omissions and substitutions and changes in the form and details of the disclosed apparatus, and in its operation, may be made by those skilled in the art without departing from the spirit of the invention. It is the intention, therefore, to be limited only as indicated by the scope of the claims appended hereto.

For example, although the present invention has been described with reference to a particular catheter handle, other catheter handles may be employed so long as they are able to provide the necessary control of the shim 66 and guide wire 52.

The shim of the catheter of the present invention may also have more than two twists thereby resulting in a catheter that can attain curves in more than three planes. The twists in the shim may also be offset by angles other than 45° and 90° so that the planes of curvature of the catheter's tip are respectively offset. The collars 86 may be replaced with any other structure or means or arrangement for preventing unintended slippage or displacement of the guide wire.

Additionally, although the steerable catheter of the present invention is expressly disclosed for use in sensing electrical signals in body tissues and for applying electric power to such tissues, the catheter design may be readily and suitably modified for use in other applications such as in the pumping of fluids (liquid or gas) into or out of a patient. In such an alternate utility, the electrical contact plates 64 in the catheter's tip portion 54, the electrical conductors 62 and the electrical power source may be eliminated. Instead, one or a plurality of holes or apertures may be provided in the catheter's tip portion 54, and an appropriate pump or the like may be connected to the rearward end of tube 14 so as to provide suction to evacuate fluid from the patient or to positively pump fluid and/or medications into the patient. Similarly, optical fibers can be provided instead of, or in addition to, the electrical conductors 62. In such an embodiment one or more optical fibers may be connected to a light source, such as a laser, while one or more other optical fibers are connected to a video camera and/or similar viewing or recording devices. Alternatively, a longitudinally movable rigid cable may protrude through a bore or opening in the catheter's tip portion 54 for removal of patient tissue for biopsy. Any one or more of these alternative utilities or embodiments may also be combined one with another for a particular use contemplated or intended for the catheter of the present invention. Finally, and as should be apparent to those skilled in the art, the dimensions herein mentioned relate to one particular catheter size in the particular embodiment(s) of the inventive apparatus shown in the drawings and are disclosed solely by way of example and should not, therefore, be understood as an intended limitation on the scope of the invention.

What is claimed is:

1. A tip-deflectable, steerable catheter comprising:
   a catheter handle having a first body and a second body, said second body being slidably mounted to and for selective longitudinal sliding movement relative to said first body;
   an elongated catheter tube having longitudinally spaced apart proximal and distal ends, said proximal end of said catheter tube being fixedly attached to said second body of said catheter handle;
   a catheter tip portion carried at said distal end of said catheter tube and having a distal end most remote from said handle; and
   an elongated, substantially flat planar shim having longitudinally spaced apart proximal and distal ends disposed within said catheter tip portion, said shim having a lateral twist between said proximal and distal ends of said shim, said shim distal end being attached to said distal end of said catheter tip portion and to said catheter handle first body, and said shim proximal end being attached to said second body of said catheter handle so that longitudinal movement of said catheter tube distal end as said second body is selectively moved longitudinally toward said catheter tip portion relative to said handle first body causes said proximal end of said shim to move correspondingly longitudinally and said attachment of said shim to said catheter handle body causes three-dimensional tip-deflecting curvature of said catheter tip portion in accordance with said selective longitudinal movement of said second body relative to said first body.

2. The steerable catheter of claim 1, wherein:
   said catheter tube includes a central lumen defined in and extending longitudinally from said proximal end to said distal end of said catheter tube;

said catheter tip portion includes a central lumen defined in and extending longitudinally along said tip portion, said central lumen of said catheter tip portion being aligned with and connected to said central lumen of said catheter tube; and said shim being disposed within said central lumen of said catheter tip portion.

3. The steerable catheter of claim 2, wherein said shim distal end is attached to said catheter handle first body by a pull cable having a distal end and a proximal end and extending slidably within and along said central lumen of said catheter tube and said catheter tip portion, said distal end of said pull cable being fixedly attached to the distal end of said shim, and said proximal end of said pull cable being attached to said first body.

4. The steerable catheter of claim 1, further comprising a collar fixedly mounted to said shim and through which said pull cable is slidably mounted.

5. The steerable catheter of claim 1, wherein the lateral twist of said shim extends along substantially the entire length of said shim.

6. The steerable catheter of claim 5, wherein said proximal end of said shim is twisted approximately 45° relative to the distal end of said shim.

7. The steerable catheter of claim 1, wherein the lateral twist of said shim comprises a twist of approximately 90° between the distal and proximal ends of said shim.

8. The steerable catheter of claim 1, wherein said shim includes two longitudinally displaced lateral twists.

9. The steerable catheter of claim 1, further comprising curvature locking means on said handle and operable for locking said catheter tip portion into a selected three-dimensional curvature.

10. In a tip deflectable catheter having an elongated catheter tube extending from a proximal end to a distal end, a selectively-deflectable catheter tip portion carried on the catheter tube distal end and extending from a proximal end to a distal end most remote from said catheter tube, a shim disposed within the catheter tip portion, and adjustable means connected to the distal end of the shim and to the proximal end of the shim and selectively operable by a user for varying a distance between the distal and proximal ends of the shim and thereby effecting selective deflection of the tip portion, said shim comprising an elongated, substantially flat member having a transverse twist defined therein for providing three-dimensional deflection of said catheter tip portion in accordance with selective user operation of said adjustable means.

11. In a tip deflectable catheter in accordance with claim 10, said shim having a transverse twist located at a predetermined location along the elongation of said shim so as to define a first section and a second section of said shim, said first and second sections between separated by said transverse twist and each of said first and second sections being substantially flat and lying in a plane separate and distinct from the other of said first and second sections.

12. In a tip deflectable catheter in accordance with claim 10, wherein said transverse twist extends along at least a portion of the elongation of said shim.

13. In a tip deflectable catheter in accordance with claim 10, wherein said adjustable means comprises a wire connected to said shim distal end and extending within and along the catheter tip portion and the catheter tube, further comprising retention means proximate said transverse twist for positionally maintaining said wire in relatively close proximity to said transverse twist.

14. In a tip deflectable catheter in accordance with claim 13, wherein said retention means is secured to said shim proximate said transverse twist.

15. In a tip deflectable catheter in accordance with claim 14, wherein said retention means includes a bore through which said wire guidedly extends for longitudinal displacement of the wire relative to and through said bore.

* * * * *